United States Patent [19]

Vaughn et al.

[11] Patent Number: 5,569,256
[45] Date of Patent: Oct. 29, 1996

[54] SURGICAL RESECTION TOOL WITH A DOUBLE QUICK RELEASE

[75] Inventors: William J. Vaughn, Fort Worth; Ray E. Umber, Arlington; William E. St. Clair, Colleyville; Larry D. Estes, North Richland Hills; Glenn T. Carlson, Fort Worth, all of Tex.

[73] Assignee: Midas Rex Pneumatic Tools, Inc., Fort Worth, Tex.

[21] Appl. No.: 386,927

[22] Filed: Feb. 10, 1995

[51] Int. Cl.$^6$ .......................... A61B 17/14; A61B 17/32
[52] U.S. Cl. ............................ 606/80; 606/180; 279/75
[58] Field of Search .................. 606/80, 170, 180; 279/75, 19.4, 19.5, 904, 905

[56] References Cited

U.S. PATENT DOCUMENTS

| Re. 27,032 | 1/1971 | Hall . | |
|---|---|---|---|
| 3,847,154 | 11/1974 | Nordin | 606/180 |
| 4,071,029 | 1/1978 | Richmond et al. | 606/180 |
| 4,963,155 | 10/1990 | Lazzeri et al. . | |
| 5,028,181 | 7/1991 | Jenkins et al. | 279/75 X |
| 5,265,343 | 11/1993 | Pascaloff . | |
| 5,437,465 | 8/1995 | Vogele et al. | 279/75 X |

OTHER PUBLICATIONS

Meisinger's Chirurgie Surgery Sales Brochure.
OSM's Chirurgie Surgery Sales Brochure.
The Hall Surgical Drill Instruction Manual.
YNET Motordrill Operating Procedures Pamphlet.
MicroAire Surgical Instruments Sales Brochure.
Mednext Sales Brochure.
Stryker Instruments Sales Brochure.
One page advertisement brochure for Hall Surgical.

*Primary Examiner*—Michael Powell Buiz
*Assistant Examiner*—Patrick W. Rasche
*Attorney, Agent, or Firm*—James E. Bradley

[57] ABSTRACT

A surgical resection tool of the type having a rotary motor, a dissecting tool and a bearing tube is provided with dual quick releases for quickly releasing and latching dissecting tools and bearing tubes to expedite tooling changes during surgical procedures. The surgical resection tool preferably has a canted centerline in which the centerline for the rotary motor is canted with respect to the centerline for the dissecting tool and the bearing tube to provide an ergonomic shape for holding the resection tool. In a preferred embodiment, the two quick releases are provided by collet type latches having latching balls and slidable sleeves. The slidable sleeves are coupled together for selectively moving to a latching position where latching balls are pressed into grooves formed into dissecting tools and bearing tubes to latch a dissecting tool and a bearing tube into the resection tool. The slidable sleeves are moved to a second position to allow the latching balls to release from within the grooves so that dissecting tools and bearing tubes may be quickly replaced.

24 Claims, 3 Drawing Sheets

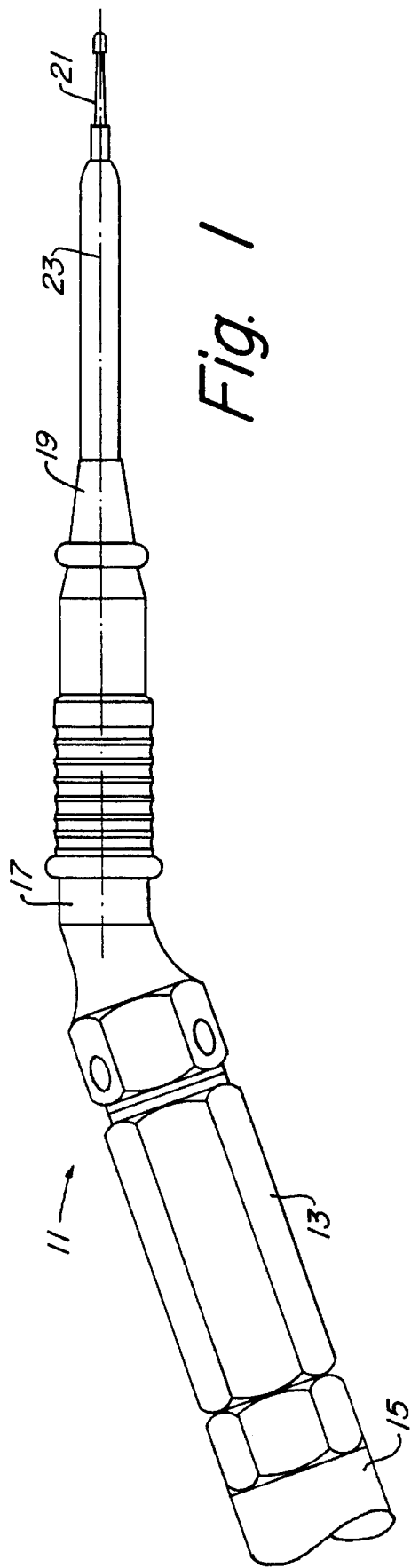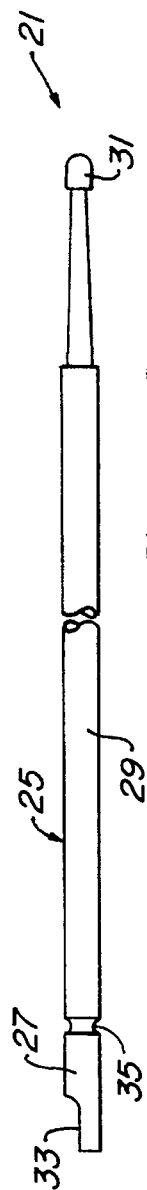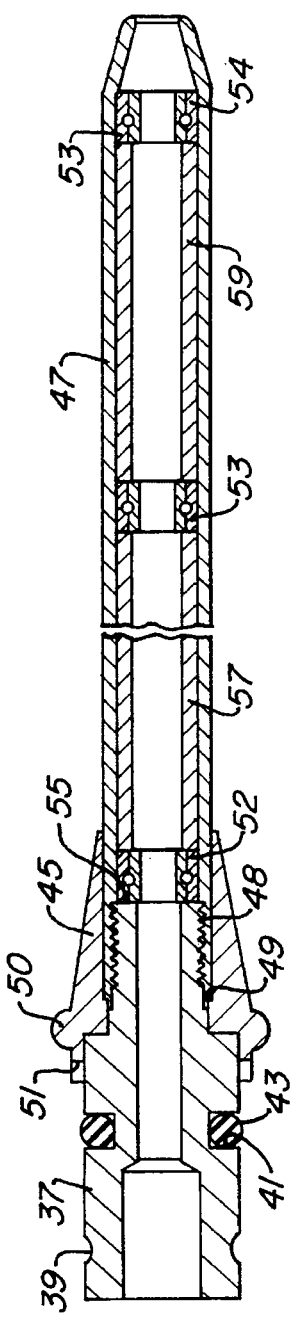

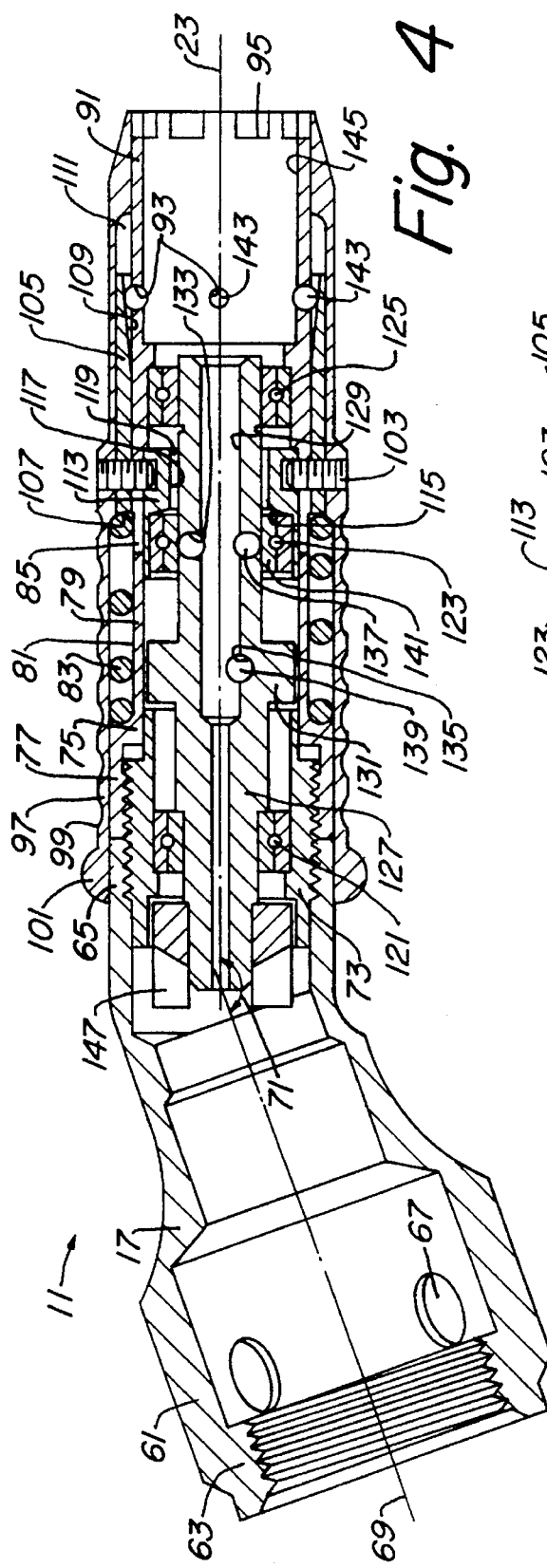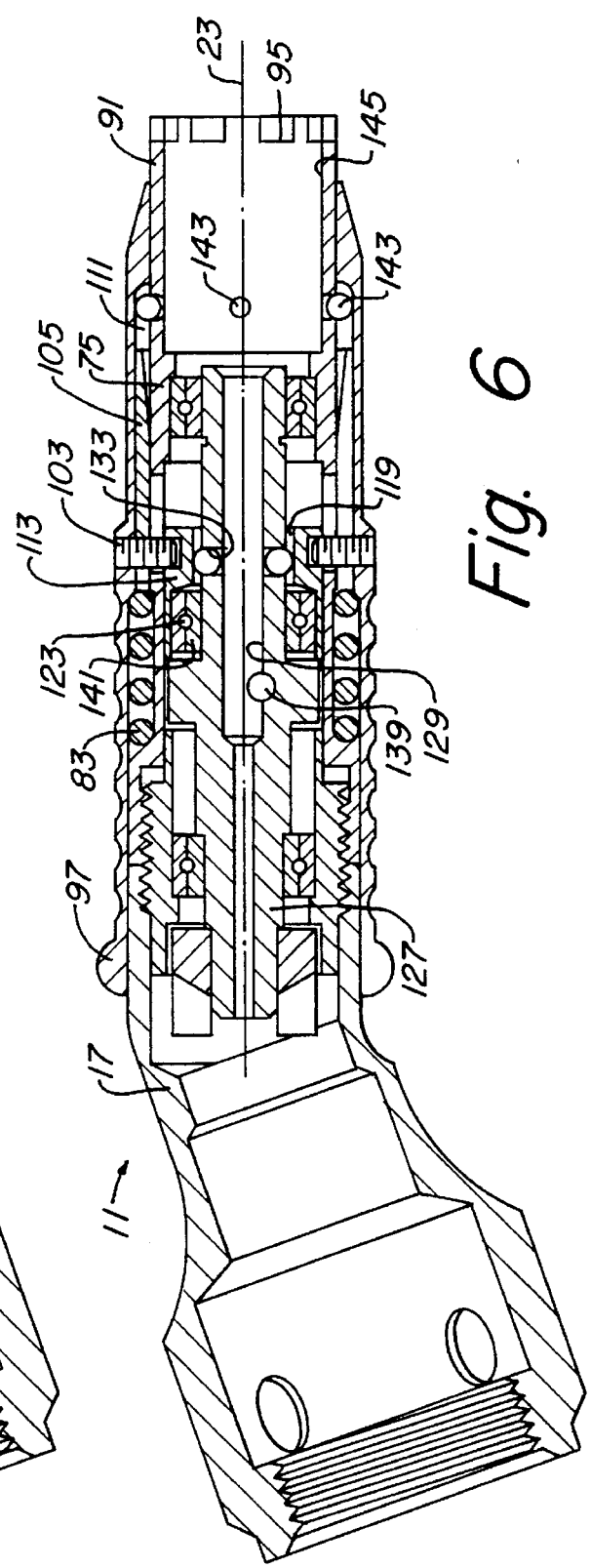

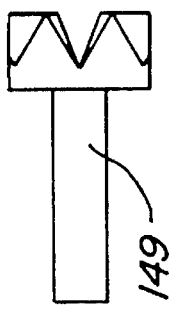
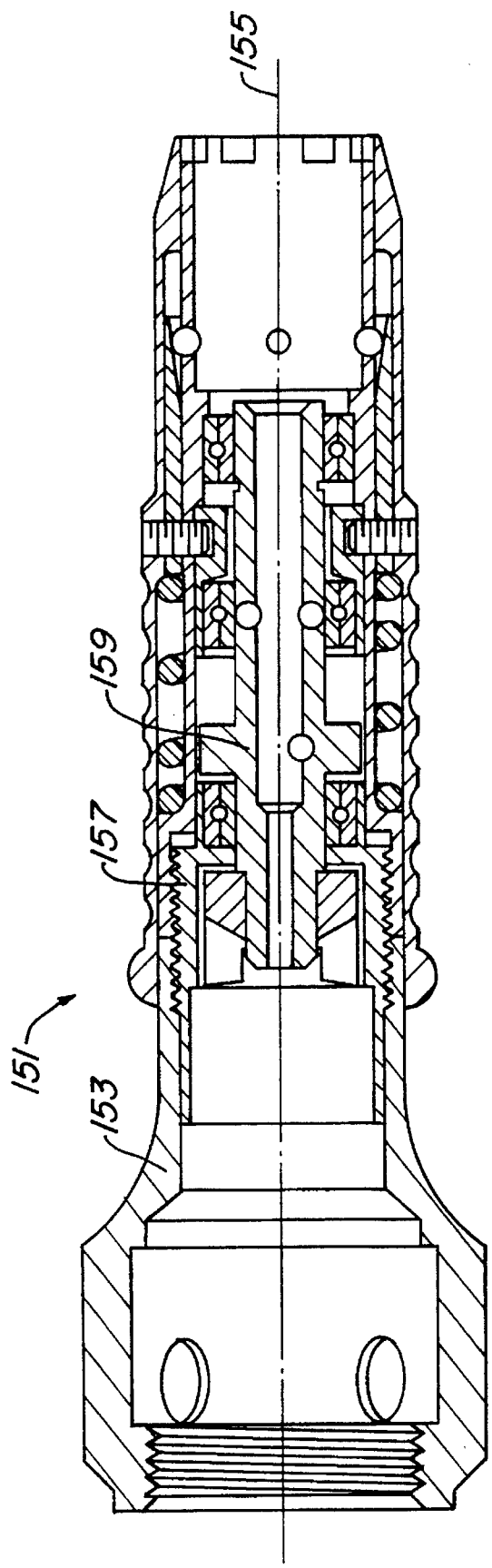
Fig. 5
Fig. 7

SURGICAL RESECTION TOOL WITH A DOUBLE QUICK RELEASE

BACKGROUND OF THE INVENTION

1. Field of Art

This invention relates in general to surgical tools, and in particular to rotary powered surgical resection tools.

2. Description of the Prior Art

Surgical resection tools have been used for resecting, or cutting, bone and tissue during surgical procedures. Many such tools employ pneumatic or electric motors to rotate the cutting elements of these tools. In their most basic form, such surgical instruments comprise a rotary motor having a rotary shaft, or spindle, a dissecting tool having a cutting element which is rotated by the motor, a bearing tube to surround and support the dissecting tool, and a means for connecting the dissecting tool to a spindle of the motor. A standard type of collet chuck is typically mounted to the motor spindle for securing the dissecting tool to the motor. The collet chuck is mounted within a base of a stationary housing which is threadingly secured to a stationary portion of the motor. The bearing tube is mounted to the base, typically by a threaded connection.

In order to replace a dissecting tool, the base has to be unscrewed from the motor so that the collet chuck can be accessed. The bearing tube is usually secured to the base by a threaded connection, and is often sized so that it cannot be removed from over the resecting tool because of the size of the cutting element. Wrenches or other hand tools are used to threadingly secure and release bearing tubes from the base, and the base from the motor. Collet chucks for securing the dissecting tool to the motor are usually provided with a collet nut and slotted sleeve, which are mounted to the rotary motor spindle. The collet nut must be rotated for some distance around the slotted sleeve for the dissecting tool to be released for removal from the slotted sleeve and the spindle. Usually a wrench or other type of hand tool is used to rotate the collet nut. Once the dissecting tool is removed and replaced, the collet nut is rotated to clamp the dissecting tool within the slotted sleeve and to the spindle. The base is also rotated to secure the bearing tube to the stationary portion of the motor.

It is often necessary to replace dissecting tools many times during a given surgical procedure. This requires that the above procedure be carried out frequently. It is also often required that bearing tubes be replaced with other bearing tubes of various lengths and diameters to accommodate dissecting tools of various sizes. Replacing the bearing tube requires that another threaded connecting be broken and then made up. Replacing dissecting tools and bearing tubes is usually a time consuming task since wrenches and rods are often necessary to break and make up the threaded connections securing dissecting tools and bearing tubes to surgical resection tools. What is needed is a means for coupling dissecting tools, bases and bearing tubes within a surgical resection tool so that the dissecting tools and bearing tubes may be quickly and easily removed and replaced.

SUMMARY OF THE INVENTION

A surgical resection tool of the type having a rotary motor, a dissecting tool and a bearing tube is provided with dual quick releases for quickly releasing and latching dissecting tools and bearing tubes to expedite tooling changes during surgical procedures. The surgical resection tool preferably has a canted centerline in which the centerline for the rotary motor is canted with respect to the centerline for the dissecting tool and the bearing tube to provide an ergonomic shape for holding the resection tool. In a preferred embodiment, the two quick releases are provided by collet type latches having latching balls and slidable sleeves. The slidable sleeves are coupled together for selectively moving to a latching position where latching balls are pressed into grooves formed into dissecting tools and bearing tubes to latch a dissecting tool and a bearing tube into the resection tool. The slidable sleeves are moved to a second position to allow the latching balls to release from within the grooves so that dissecting tools and bearing tubes may be quickly replaced.

The two collet type latches of the preferred embodiment secure the dissecting tool and bearing tube from being pulled forward and from within the resection tool. Torque is transferred to the dissecting tool by means of a flat formed into a rearward end of a shank of the dissecting tool. The flat is spaced apart on the shank from the groove into which the latching balls extend. The bearing tube is included within an attachment assembly which has rearwardly facing castellations which mate with forward facing castellations formed into a forward end of a stationary housing of the resection tool to nonrotatably secure the bearing tube to the stationary housing.

BRIEF DESCRIPTION OF THE DRAWINGS

The novel features believed characteristic of the invention are set forth in the appended claims. The invention itself however, as well as a preferred mode of use, further objects and advantages thereof, will best be understood by reference to the following detailed description of an illustrative embodiment when read in conjunction with the accompanying drawings, wherein:

FIG. 1 is a perspective view of a surgical resection tool made according to the present invention;

FIG. 2 is a perspective view of a dissecting tool for use with a surgical resection tool made according to the present invention;

FIG. 3 is a longitudinal section view of a bearing tube attachment assembly made according to the present invention;

FIG. 4 is a longitudinal section view of a main body portion for a surgical resection tool according to the present invention, with the components thereof disposed in a latching position for securing a dissecting tool and a bearing tube attachment assembly to the surgical resection tool;

FIG. 5 is a perspective view of a gear for use in the surgical resection tool of the present invention;

FIG. 6 is a longitudinal section view of the main body portion for the surgical resection tool of FIGS. 1 and 4, with the movable components thereof disposed in an unlatched position for removal and insertion of dissecting tools and bearing tube attachment assemblies; and FIG. 7 is a longitudinal section view of a main body portion for a surgical resection tool of an alternative embodiment of the present invention.

DETAILED DESCRIPTION OF THE PREFERRED EMBODIMENT

FIG. 1 is a perspective, elevational view depicting surgical resection to 11 which is made according to the present invention. Resection tool 11 includes rotary motor 13, which is connected to air supply 15. Resection tool 11 further includes stationary housing 17, bearing tube attachment assembly 19 and dissecting tool 21. Resection tool 11 has a central axis 23 extending through resection tool 11. Rotary motor 13 provides power for rotating dissecting tool 21. Dissecting tool 21 is rotatably secured within stationary housing 17 for rotating around central axis 23. Bearing tube attachment 19 provides a bearing tube for rotatably supporting and directing dissecting tool 21.

FIG. 2 is a perspective view depicting dissecting tool 21, which is of a type for use within resecting tool 11. Dissecting tool 21 includes elongated shank 25 having a proximal end portion 27 and intermediate portion 29. Cutting head 31 provides a cutting element on a forward end of shank 25 for rotating to resect bone and tissue. Flat 33 is provided by an indentation into the end tip of elongated shank 25 at proximal end portion 27. Groove 35 is an indentation into shank 25 which circumferentially extends around proximal end portion 27, in a spaced apart relation to flat 33.

FIG. 3 is a longitudinal section view of bearing tube attachment assembly 19. Assembly 19 includes rearward end portion 37. A circumferentially extending latch groove 39 is formed into the exterior of rearward portion 37. O-ring groove 41 is also formed exteriorly into and circumferentially extends around rearward end portion 37 for receipt of o-ring 43. It should be noted that o-ring 43 is not provided for sealing in this embodiment of the present invention, but rather provides a frictional means for retaining rearward end portion 37 within a cylindrical interior profile of surgical resection tool 11 after a latching means is released from securing attachment assembly 19 within resection tool 11. Thus, a slightly greater force is required to remove attachment assembly 19 from surgical tool 11 than is required to remove dissecting tool 21. This allows bearing tube attachment assembly 19 to remain in place while dissecting tools are removed and replaced when assembly 19 is not being replaced.

Attachment assembly 19 further includes tapered sleeve 45 and extension tube 47. Sleeve 45 is secured by threaded connection 48 to extension tube 47. Tapered sleeve 45 includes a forward facing shoulder 49 which engages a rearward end of extension tube 47, and sleeve 45 is entrapped between the rearward end of tube 47 and the forward end of portion 37 of assembly 19. Protuberance 50 circumferentially extends exteriorly from tapered sleeve 45. Tapered sleeve 45 provides a rearward end of bearing tube 19 which includes rearward facing castellations 51.

A rearward bearing 52, intermediate bearing 53 and forward bearing 54 are provided interiorly within bearing tube 19 for rotatably supporting intermediate portion 29 of shank 25 for dissecting tool 21 (shown in FIG. 2). Shoulder 55 is defined by a forward end of rearward end portion 37 and holds rearward bearing 52 in place. Spacers 57 and 59 are provided by sleeves which are mounted interiorly within extension tube 47 for spacing bearings 52, 53 and 54 apart within bearing tube assembly 19.

Various bearing tube attachment lengths may be provided by replacing extension tube 47 with extension tubes of different lengths. Extension tubes and bearings of different internal diameters may also be provided to accommodate dissecting tool shanks of various diameters. Bearing tubes should be sized to match particular diameters and lengths of resection tools in surgical procedures. It should also be noted that intermediate bearing 53 may be omitted for short extension tubes, and that additional bearings may be desirable for extension tubes which are longer than extension tube 47.

Referring to FIGS. 2 and 3, some dissecting tools may be made with cutting heads that are sufficiently smaller than the shanks so that the cutting heads will pass through a bearing tube sized for supporting the shanks. For such dissecting tools, a bearing tube attachment assembly will pass over the cutting head and may be installed onto a surgical resection tool, such as resection tool 11, after the dissecting tool has been installed. However, if the cutting head for the resection tool will not pass through the bearing tube, the rearward shank of the dissecting tool must be passed through the forward of the bearing tube for mounting to the surgical resection tool.

FIG. 4 is a longitudinal section view of the main body portion of surgical resection tool 11, shown in a latched position. The main body portion for surgical resection tool 11 includes stationary housing 17. Stationary housing 17 includes attachment base 61 having a threaded rearward end for securing to a stationary portion of rotary motor 13 (shown in FIG. 1). Base 61 further includes a threaded forward end 65. Holes 67 extend through the side wall of attachment base 61 for passing a rod or other hand tool which is used to transfer torque to attachment base 61 for threadingly securing base 61 onto rotary motor 13 (shown in FIG. 1).

Attachment base 61 has an attachment base central axis 69 which is disposed at an angle 71 to central axis 23. Dual central axes 23, 69 together provide a canted centerline for surgical resection tool 11. This canted centerline design provides a more ergonomic, contoured shape for surgical resection tool 11 than prior art straight centerline designs for surgical resection tools, in which a central axis, or centerline, for an attachment base and rotary motor are directly aligned along a straight line with the central axis of rotation for dissecting tools. In the preferred embodiment of the present invention, the canted centerline provided by the canted central axes 23, 69 is at an angle 71, which is an obtuse angle measuring approximately 160 degrees.

Stationary housing 17 further includes exteriorly threaded sleeve 73 and stationary sleeve 75. Stationary sleeve 75 includes rearward section 77 having interior threads for securing stationary sleeve 75 to exterior threaded sleeve 73. Exteriorly threaded sleeve 73 is secured to threaded forward end 65 of attachment base 61. Exterior threaded sleeve 73 and stationary sleeve 75 are cylindrical sleeves which are concentrically aligned and which are co-axially disposed with central axis 23.

Stationary sleeve 75 further includes intermediate section 79 having two elongated slots 85 formed therein to longitudinally extend in parallel to central axis 23. Slots 85 are circumferentially aligned around sleeve 75 to extend laterally through opposites sides of the sidewall for sleeve 75, in transverse relation to central axis 23. Profile 81 is exteriorly formed into sleeve 75, and circumferentially extends around intermediate portion 79 for receipt of bias spring 83. Profile 81 also extends longitudinally along sleeve 75 in parallel with central axis 23. Stationary sleeve 75 further includes forward section 91, into which four holes 93 (three shown) laterally extend through the side wall of stationary sleeve 75, in transverse relation to central axis 23. Holes 93 are circumferentially spaced apart around forward section 91. Forward facing castellations 95 are formed into the end tip of forward section 91.

Exterior sleeve 97 is exteriorly mounted about stationary sleeve 95. Sleeve 97 includes a rippled exterior surface 99 and thumb knurl 101, which is provided by an outwardly extending protuberance on the rearward end thereof.

Rippled exterior surface 99 and knurl 101 provide a means for gripping exterior sleeve 97. Two set screws 103 threadingly secure within exterior sleeve 97 and into latch actuator sleeve 105.

Latch actuator sleeve 105 includes a rearward end 107 which provides a shoulder for abutting bias spring 83, and an interiorly tapered forward end 109. A forward annular cavity 111 is defined between the forward interiorly tapered end 109 of actuator sleeve 105, a forward interior portion of exterior sleeve 97, and an exterior surface of stationary sleeve 75.

Collet 113 is disposed within stationary sleeve 75 and is secured to latch actuator sleeve 105 and exterior sleeve 97 by the two set screws 103. Collet 113 has rearward shoulder 115, and internal diameter 117, which is defined on a forward end. Collet shaft 127 extends within internal diameter 117. Rearward annular cavity 119 is defined between internal diameter 117 of collet 113, and an exterior surface for collet shaft 127. Bearings 121 and 125 are mounted within stationary sleeve 75, and bearing 123 is mounted within collet 113, adjacent to rearward shoulder 115. Bearing 123 and collet 113 together provide a collet assembly for sliding over an exterior surface of collet shaft 127.

Collet shaft 127 is rotatably secured within stationary sleeve 75 by bearings 121, 123 and 125. Collet shaft 127 includes central bore 129, which is co-axially aligned with central axis 23. Exterior protuberance 131 extends from an exterior of collet shaft 127, and provides forward and rearward facing shoulders. Two holes 133 are circumferentially aligned on opposite sides of collet shaft 127, and extend laterally through collet shaft 127 in transverse relation to central axis 23. A singular hole 135 extends through the collet shaft 127 and connects with central bore 129. A centerline for hole 135 extends laterally through collet shaft 127 in transverse relation to central axis 23, and is offset from intersecting central axis 23.

Two holes 133 are radially aligned on opposite sides of central axis 23. Two balls 137 are disposed within the two holes 133 and provide locking members, which will roll around axes of rotation parallel to central axis 23. Balls 137 are preferably made from steel, and may be provided by balls of the type used in ball bearings. The two holes 133 are preferably tapered to each have an inward diameter which is smaller than an outward diameter for holes 133 (only one diameter shown) so that balls 137 will not fall into central bore 129 and out the forward end of collet shaft 127.

A cylindrical pin 139 extends through the singular hole 135 and also provides a locking member for securing dissecting tool 21 to resection tool 11. Cylindrical pin 139 also extends within central bore 129, and has a centerline which extends in transverse relation to central axis 23. The centerline for pin 139 is offset so that is does not intersect the centerline for central bore 129, which is defined along central axis 23. Pin 139 provides a lock member which serves as a drive member for transferring torque from collet shaft 127 to dissecting tool 21. In other embodiments of the present invention, other types of members may be used in place of pin 139 for transferring torque to flat 33 of dissecting tool 21, such as a set screw which extends into central bore 129 at a right angle to the centerline of pin 139 for engaging flat 33 at a right angle.

Inner race 141 of bearing 123 provides a retaining member for retaining balls 137 within holes 133 so that they extend from holes 133 into central bore 129. Collet 133 and bearing 123 together provide a collet assembly for selectively sliding over the forward end of collet shaft 127 to align either internal diameter 117 for the forward end of collet 133 or race 141 adjacent to holes 133 and balls 137. When race 141 is aligned laterally adjacent to holes 133, balls 137 are locked into a locked position wherein balls 137 are retained to extend from holes 133 into central bore 129. When the internal diameter 117 is aligned laterally adjacent to holes 133, balls 137 may move into an unlocked position in which they extend into the gap between collet shaft 127 and collet 113 rather than into central bore 129. This gap between collet 113 and collet shaft 127 is defined by rearward annular cavity 117.

Four balls 143, like balls 137, may be provided by steel ball bearings. Balls 143 provide latching members which are secured within holes 93 in forward section 91 of the stationary sleeve 75. Holes 93 are preferably formed with a taper having a smaller inward diameter than an outer diameter for each of holes 93 (only one diameter shown) so that balls 143 will remain within holes 93, and will not fall out the forward end of stationary sleeve 75. Latch actuator sleeve 105 is biased into a forward position by bias spring 83 so that interiorly tapered forward end 109 retains the four ball bearings 143 within the four holes 93 and balls 143 extend from holes 93 into interior profile 145, which is interiorly defined within forward section 91 of stationary sleeve 75.

Gear 147 is rigidly mounted to a rearward end of collet shaft 127. Gear 147 is part of a power transfer means for receiving torque from rotary motor 13 (shown in FIG. 1) and transferring the torque to collet shaft 127.

FIG. 5 is a perspective view of gear 149 for securing within a standard chuck on the spindle a rotary motor, such as rotary motor 13 (shown in FIG. 1). Gear 149 is part of the power transfer means for transferring torque from the spindle for rotary motor 13 (shown in FIG. 1) to gear 147 and collet shaft 127.

FIG. 6 is a longitudinal section view depicting the main body portion for surgical resection tool 11 in a released position, in which dissecting tools and attachment tube assemblies made according to the present invention may be inserted and removed from resection tool 11. Exterior sleeve 97, actuator sleeve 104, collet 113 and bearing 123 have been moved rearward so that balls 133, 143 are free to extend within rearward annular cavity 119 and forward annular cavity 111, respectively. Pin 139 remains in the same position extending within collet shaft 127 and central bore 129.

Referring to FIGS. 2, 3 and 6, dissecting tool 21 and bearing tube attachment assembly 19 are installed into surgical resection tool 11 when tool 11 is disposed in the unlatched position shown in FIG. 6. Dissecting tool 21 is inserted within central bore 129, with flat 33 aligning against pin 37 and groove 35 aligned adjacent to balls 133. Bearing tube attachment assembly 19 is inserted into the forward end of stationary sleeve 75. Profile 145 is sized for receiving rearward end portion 37 of tube 19. 0-ring 43 will provide a means for frictionally holding attachment tube 19 within profile 145 until tube 19 is latched into position. Forward facing castellations 95 extend and mesh with rearward facing castellations 51 to prevent rotation of tube 19. Groove 39 are is aligned adjacent to balls 143.

Exterior sleeve 97 may then be released and bias spring 83 will urge sleeve 97, actuator sleeve 105, collet 113, and bearing 123 to slide forward and press balls 133, 143 inwardly toward central axis 23. Balls 133 will then extend within groove 35 of shank 19 for dissecting tool 21 to latch dissecting tool 21 within central bore 129. Balls 143 will also extend toward central axis 23, and engage within groove 39 to latch bearing tube 19 within profile 145. Surgical resection 11 may then be operated for resecting bone.

In operation, air is passed through rotary motor 13 to power motor 13. Rotary motor 13 rotates gear 149 (shown in FIG. 5), which is secured by a standard collet chuck to the spindle for a rotary motor 13. Gear 149 is meshed with gear 147 so that rotating gear 149 transfers torque to gear 147. This rotates collet shaft 127. Rotation of collet shaft 127 transfers torque to pin 139, which transfers torque to flat 23 formed into shank 25 to rotate dissecting tool 31. Thus, cylindrical pin 139 provides a drive member for transferring torque to dissecting tool 31.

When a surgeon desires to change to a different dissecting tool, often a different size bearing tube is required. The dual quick release feature of surgical resection tool 11 of the present invention is then operated to simultaneously release both attachment tube 19 and dissecting tool 21. The surgeon grips exterior sleeve 97 and slides it rearward to urge latch actuator sleeve 105, collet 113 and bearing 123 rearward against the biasing force of spring 83. Then, balls 133 are free to extend into annular cavity 119 to release dissecting tool 21, and balls 143 are free to extend into annular cavity 111 to release bearing tube 19. Dissecting tool 21 and bearing tube 19 may then be pulled forward and removed from within central bore 129 and profile 145, respectively. Then, a selected dissecting tool and another appropriately sized bearing tube may be inserted into and latched within surgical resection tool 11.

FIG. 7 is a longitudinal section view of a portion for alternative surgical resection tool 151, which incorporates some of the features of the present invention. Attachment base 153 is co-axially aligned with central axis 155, rather than being canted to the central axis for surgical resection tool 151 at an obtuse angle. Various portions of surgical resection tool 151 are similar to resection tool 11, except that exterior threaded sleeve 157 and collet shaft 159 are provided with shorter longitudinal lengths than threaded member 73 and collet shaft 127 (shown in FIG. 4). Surgical resection tool 151 is otherwise substantially identical to surgical resection tool 11.

Surgical resection tools made according to the present invention provide advantages over prior art surgical resection tools. Dissecting tools and bearing tubes may be quickly released and replaced by means of the dual quick release feature of a surgical resection tool made according to the present invention. Dissecting tools and matched bearing tubes are simultaneously released by sliding an exterior sleeve rearward. The exterior sleeve is spring biased into a forward position so than when it is released it will returned to a latching position to secure a dissecting tool and bearing tube within the surgical resection tool. Thus, dissecting tools and bearing tubes may be quickly replaced and interchanged while performing surgical procedures. Further, a surgical tool made according to the present invention may incorporate the canted centerline feature, which provides an ergonomic grip for surgeons.

Although the invention has been described with reference to a specific embodiments, this description is not meant to be construed in a limiting sense. Various modifications of the disclosed-embodiment as well as other alternative embodiments of the invention will become apparent to persons skilled in the art upon reference to the description of the invention. It is therefore contemplated that the appended claims will cover any such modifications or embodiments that fall within the true scope of the invention.

We claim:

1. In a surgical resection tool of the type having a rotary motor which includes a spindle and a stationary portions, the spindle being rotatable relative to the stationary portion, a stationary member which is rigidly secured to the stationary portion of the rotary motor and which longitudinally extends and defines a central axis for the tool, a collet shaft which has a central bore formed therein and which is rotatably secured to the stationary member for rotating about the central axis with the central bore coaxially aligned with the central axis, a dissecting tool which includes a cutting head for rotating to resect bone and a shank with a proximal end portion secured within the collet shaft in coaxial relation to the central bore, a bearing tube nonrotatably secured to the stationary member for rotatably supporting an intermediate portion of the shank for the dissecting tool, and a power transfer means for securing the rotary motor to the collet shaft and transferring torque therebetween, the improvement comprising in combination:

the shank having at least one indentation formed therein to laterally extend into the shank in transverse relation to the central axis;

the collet shaft having a hole formed therein to laterally extend into the collet shaft, the hole aligned with the at least one indentation formed into the shank, and the hole extending in transverse relation to the central axis;

a locking member extending within both the hole in the collet shaft and the indentation in the shank to secure the dissecting tool to the collet shaft, and the locking member being moveable away from the central axis to remove the locking member from extending within the at least one indentation in the shank;

locking means movably secured to the collet shaft for retaining the locking member within both the hole in the collet shaft and the at least one indentation in the shank, and for selectively moving relative to the collet shaft to release the locking member for moving transversely away from the central axis and from within the at least one indentation in the shank to selectively release the dissecting tool for removal from the collet shaft;

the bearing tube having a latch indentation which laterally extends into the bearing tube in transverse relation to the central axis;

the stationary member having an aperture laterally extending therein in transverse relation to the central axis;

a latching member extending within both the aperture in the stationary member and the latch indentation in the bearing tube to nonrotatably secure the bearing tube to the stationary member, and the latching member being moveable in transverse relation to the central axis to remove the latching member from extending within one of the aperture and the latch indentation; and latching means movably secured to the stationary member for retaining the locking member within both the aperture in the stationary member and the latch indentation in the bearing tube, and for selectively moving relative to the stationary member to release the latching member for moving in transverse relation to the central axis and from within the one of the aperture and the latch indentation to release the bearing tube for removal from the stationary member.

2. The surgical resection tool according to claim 1, further comprising:

coupling means connected to both the locking means and the latching means for simultaneously moving both the locking means and latching means in response to moving the coupling means, to simultaneously release the bearing tube for removal from the stationary member and the dissecting tool for removal from the collet shaft.

3. The surgical resection tool according to claim 1, wherein at least one of the latching member and the locking member comprises a ball bearing.

4. The surgical resection tool according to claim 1, wherein the locking means and the latching means are urged into latching positions by a biasing means.

5. The surgical resection tool according to claim 1, wherein the stationary member is a cylindrical sleeve which is concentrically disposed around the central axis.

6. The surgical resection tool according to claim 1, wherein the latching means and the locking means are cylindrical sleeves which are concentrically disposed around the central axis.

7. The surgical resection tool according to claim 1, further comprising:

a gripping means secured to a rearward end for the bearing tube for frictionally securing the bearing tube to the stationary member, when the latching means is selectively moved to release the latching member for moving from the latch indentation in the bearing tube and release the bearing tube for removal from the stationary member.

8. The surgical resection tool according to claim 1, further comprising:

an o-ring secured to a rearward end for the bearing tube for fictionally securing the bearing tube in relation to the stationary member when the latching member is released from securing the bearing tube within the stationary member.

9. The surgical resection tool according to claim 1, wherein:

the rotary motor includes a power spindle which is coaxially disposed with a central motor axis; and the central motor axis extends at a substantially obtuse angle to the central axis about which the shank for the dissecting tool rotates.

10. In a surgical resection tool of the type having a rotary motor, a dissecting tool secured to the rotary motor for rotating to resect bone and a bearing tube for rotatably supporting the dissecting tool, wherein a rearwardly disposed portion of a shank for the dissecting tool is coaxially disposed with a central axis for the surgical resection tool and includes indentations formed therein for securing the dissecting tool within the surgical resection tool, the improvement comprising in combination:

the bearing tube having a latch indentation which laterally extends into a rearward portion of the bearing tube in transverse relation to the central axis;

a stationary sleeve having a rearward section secured to a stationary portion of the rotary motor, and a forward section concentrically aligned with the bearing tube and through which an aperture laterally extends in transverse relation to the central axis, wherein the aperture extends through the stationary sleeve in alignment with the latch indentation formed into bearing tube;

a collet shaft rotatably supported within the stationary sleeve, the collet shaft having a central bore coaxially disposed with the central axis and the rearwardly disposed portion of the shank for the dissecting tool, and a plurality of holes which extend laterally through the collet shaft and into the central bore in transverse relation to the central axis, wherein the plurality of holes are separately aligned with the indentations on the shank;

power transfer means for securing the rotary motor to the collet shaft and transferring torque therebetween;

locking members disposed within the plurality of holes in the collet shaft and the indentations in the rearwardly disposed portion of the shank for the dissecting tool, wherein at least one of the locking members is moveable away from the central axis to remove the at least one of the locking members from extending within one of the indentations in the rearwardly disposed portion of the shank;

a collet actuator sleeve slidably secured exteriorly around the collet shaft for selectively retaining the at least one of the locking members within the one of the indentations in the shank for the dissecting tool, and for selectively moving relative to the collet shaft to release the at least one of the locking members for moving from within the one of the indentations in the shank of the dissecting tool;

a latching member disposed within the aperture in the stationary sleeve and the latch indentation on the rearward portion of the bearing tube, wherein the latching members is selectively moveable transversely in relation to the central axis and from within one of the aperture and the latch indentation to release the bearing tube for removal from the stationary sleeve; and a latch actuator sleeve slidably secured to the forward section of the stationary sleeve for selectively retaining the latching member within the latch indentation on the rearward end of the bearing tube, and for moving relative to the stationary sleeve to release the latching member from extending within the one of the aperture in the stationary sleeve and the latch indentation in the rearward portion of the bearing tube.

11. The surgical resection tool according to claim 10, further comprising:

means for simultaneously moving the latch actuator sleeve and the collet actuator sleeve in relation to the stationary sleeve and the collet shaft, respectively, to simultaneously release the latching member from extending within the latch indentation in the bearing tube and to release the at least one of the locking members from extending within the one of the indentations in the shank for the dissecting tool.

12. The surgical resection tool according to claim 10, further comprising:

an exteriorly disposed sleeve slidably secured to the stationary sleeve and rigidly secured to the latch actuator sleeve and the collet actuator sleeve for simultaneously moving the latch actuator sleeve and the collet actuator sleeve in relation to the stationary sleeve and the collet shaft, respectively, to simultaneously release, in response to moving the exteriorly disposed sleeve, the latching member from extending within the latch indentation in the bearing tube and to release the at least one of the locking members from extending within the one of indentations in the shank for the dissecting tool.

13. The surgical resection tool according to claim 10, wherein:

a second one of the indentions in the rearwardly disposed portion of the shank defines a flat which laterally extends in transverse relation to the central axis; and the locking members comprise a pin which laterally extends in transverse relation to the central axis, and against the flat for transferring torque from the collet shaft to the dissecting tool.

14. The surgical resection tool according to claim 10, wherein at least part of the locking members and the latching members comprise a plurality of ball bearings.

15. The surgical tool according to claim 10, wherein:
   a second one of the indentions in the rearwardly disposed portion of the shank defines a flat which laterally extends in transverse relation to the central axis;
   the locking members comprise a drive member which laterally extends in transverse relation to the central axis, and against the flat for transferring torque from the collet shaft to the dissecting tool; and
   the locking members and the latching members together comprise a plurality of balls.

16. The surgical resection tool according to claim 10, further comprising:
   the bearing tube having rearwardly facing castellations formed therein; and
   the forward section of the stationary sleeve having a forward end with forwardly facing castellations for mating with the rearwardly facing castellations formed into the bearing tube.

17. The surgical resection tool according to claim 10, wherein:
   the rotary motor includes a power spindle which is coaxially disposed with a central motor axis; and
   the central motor axis extends at a substantially obtuse angle to the central axis about which the shank for the dissecting tool rotates.

18. In a surgical resection tool of the type having a rotary motor, a dissecting tool secured to the rotary motor for rotating to resect bone and a bearing tube for rotatably supporting the dissecting tool, wherein a shank for the dissecting tool includes a flat which extends from a proximal end tip of the dissecting tool toward a cutting end of the dissecting tool and a groove which circumferentially extends around an exterior of the shank, spaced apart from the flat, the improvement comprising in combination:
   the bearing tube having a latch groove which circumferentially extends into a rearwardly disposed portion of the bearing tube;
   an attachment base secured to a stationary portion of the rotary motor and extending therefrom with a motor spindle disposed therein;
   a stationary sleeve having a rearward section secured to the attachment base, an intermediate section having slots which extend therethrough, and a forward section having an interior profile for receiving the bearing tube and through which apertures laterally extend in alignment with the latch groove formed into bearing tube;
   a collet shaft rotatably supported within the stationary sleeve, the collet shaft having a central bore for receiving the shank of the dissecting tool and a plurality of holes which extend laterally through the collet shaft and into the central bore, wherein separate ones of the plurality of holes are separately aligned with the flat and the groove on the shank;
   a power transfer means coupled to the motor and the collet shaft for transferring torque therebetween;
   a drive member extending through one of the plurality of holes and through the central bore in the collet shaft, aligned adjacent to the flat on the shank of the dissecting tool for transferring torque from the collet shaft to the dissecting tool;
   a plurality of collet balls disposed within the holes in the collet shaft, and selectively extending therefrom and into the groove on the shank of the dissecting tool;
   a plurality of latch balls disposed within the apertures in the stationary sleeve, and selectively extending therefrom and into the latch groove on the rearward end of the bearing tube;
   a latch actuator sleeve slidably secured exteriorly around the forward section of the stationary sleeve for selectively retaining the plurality of latch balls within the latch groove on the rearward end of the bearing tube;
   a collet actuator sleeve slidably secured exteriorly around the collet shaft for selectively retaining the plurality of collet balls within the groove in the shank for the dissecting tool;
   an exterior sleeve disposed exteriorly around the stationary sleeve and coupled to collet actuator sleeve for selectively moving the collet actuator sleeve in relation to the stationary sleeve and the collet shaft to selectively release the plurality of collet balls from within the groove in the shank for the dissecting tool; and
   coupling means extending through the slots in the intermediate section of the stationary sleeve for coupling the exterior sleeve to the collet actuator sleeve.

19. The surgical resection tool according to claim 18, wherein the exterior sleeve is coupled to both the latch and collet actuator sleeves to simultaneously move the latch and collet actuator sleeves and simultaneously release the dissecting tool and bearing tube for removal from the surgical resection tool.

20. The surgical resection tool according to claim 18, wherein the attachment base includes forward and rearward sections, and the rearward section extends at an obtuse angle to the forward section for aligning a centerline for the rotary motor, about which a power spindle for the motor rotates, at the obtuse angle to a longitudinal centerline for the central bore of the collet shaft.

21. The surgical resection tool according to claim 18, wherein the power transfer means comprises:
   a first gear mounted to the motor spindle and extending therefrom in a forward direction; and
   a second gear mounted to the collet shaft, extending therefrom in a rearward direction, and engaging the first gear for receiving torque from the first gear and the motor spindle.

22. The surgical resection tool according to claim 18, further comprising:
   the bearing tube further having an end portion with a castellated rearward end, which circumferentially extends in a spaced apart relation to the latch groove; and
   the forward section of the stationary sleeve further having a castellated forward end mated to the castellated rearward end for the bearing tube to secure the bearing tube from rotating with respect to the stationary sleeve.

23. A method for operating a surgical resection tool of the type having a rotary motor, a stationary member which longitudinally extends and defines a central axis for the tool, a collet shaft which includes a central bore and which is rotatably secured to the stationary member for rotating about the central axis with the central bore coaxially aligned with the central axis, a dissecting tool which includes a cutting head for rotating to resect bone and a shank with a proximal end portion secured to the collet shaft in coaxial relation to the central bore, a bearing tube secured to the stationary member for rotatably supporting an intermediate portion of the shank for the dissecting tool, and a power transfer means for securing the rotary motor to the collet shaft and transferring torque therebetween, the method comprising the steps of:

provided the shank with an indentation formed therein to laterally extend into the shank in transverse relation to the central axis;

providing the collet shaft with a hole formed therein to laterally extend into the collet shaft, the hole aligned with the indentation formed into the shank and extending in transverse relation to the central axis;

providing a locking member extending within both the hole in the collet shaft and the indentation in the shank to secure the dissecting tool to the collet shaft, and the locking member being moveable away from the central axis to remove the locking member from extending within the indentation in the shank;

providing a locking means movably secured to the collet shaft for retaining the locking member within both the hole and the indentation, and for selectively moving relative to the collet shaft to release the locking member for moving away from the central axis and from within the indentation in the shank to selectively release the dissecting tool for removal from the collet shaft;

providing the bearing tube with a latch indentation which laterally extends into the bearing tube in transverse relation to the central axis;

providing the stationary member with an aperture laterally extending therein in transverse relation to the central axis;

providing a latching member extending within both the aperture in the stationary member and the latch indentation in the bearing tube to secure the bearing tube to the stationary member, and the latching member being moveable transversely in relation to the central axis to remove the latching member from extending within one of the aperture and the latch indentation;

providing a latching means movably secured to the stationary member for retaining the locking member within both the aperture in the stationary member and the latch indentation in the bearing tube, and for selectively moving relative to the stationary member to release the latching member for moving transversely in relation to the central axis and from within the one of the aperture and the latch indentation to release the bearing tube for removal from the stationary member;

selectively moving the locking means in relation to collet shaft to release the locking member for moving away from the central axis and from within the indentation in the shank;

selectively moving the latching means in relation to the stationary member to release the latching member for moving in transverse relation to the central axis and from within the one of the aperture and the latch indentation;

removing the dissecting tool from within the central bore of the collet shaft;

removing the bearing tube from within the stationary member;

providing a replacement bearing tube having a replacement bearing tube latch indentation, and further providing a replacement dissecting tool having a replacement shank indentation;

inserting the replacement bearing tube into the stationary member;

inserting the replacement dissecting tool within the central bore for the collet shaft;

selectively moving the locking means in relation to collet shaft to retain the locking members within a replacement shank indentation to secure the replacement dissecting tool within the collet shaft; and selectively moving the latching means in relation to the stationary member to retain the latching member within both the aperture and the replacement bearing tube latch indentation.

24. The method according to claim 23, further comprising the steps of:

providing an external sleeve mounted exteriorly around the stationary member, and rigidly connected to both the locking means and latching means for simultaneously moving the locking means and latching means in response to moving the external sleeve; and moving the external sleeve to simultaneously move the locking means and the latching means to simultaneously release both the dissecting tool and the bearing tube for removal from the surgical resection tool.

* * * * *